(12) United States Patent
Kim et al.

(10) Patent No.: US 6,485,953 B1
(45) Date of Patent: Nov. 26, 2002

(54) ENZYME CAPABLE OF HYDORLYZING PLAQUE, MICROORGANISM PRODUCING THE SAME, AND A COMPOSITION COMPRISING THE SAME

(75) Inventors: Doman Kim, Kwangju (KR); Do-Won Kim, Kangwon-Do (KR); Soo-Jin Heo, Kwangju (KR); Su-Jin Ryu, Kwangju (KR)

(73) Assignee: Lifenza Co. Ltd., Seoul (KR)

( * ) Notice: Subject to any disclaimer, the term of this patent is extended or adjusted under 35 U.S.C. 154(b) by 47 days.

(21) Appl. No.: 09/555,535

(22) PCT Filed: Mar. 9, 2000

(86) PCT No.: PCT/KR00/00191

§ 371 (c)(1),
(2), (4) Date: Jul. 18, 2000

(87) PCT Pub. No.: WO01/66570

PCT Pub. Date: Sep. 13, 2001

(30) Foreign Application Priority Data

Mar. 9, 1999 (KR) ............................................. 99-7809

(51) Int. Cl.[7] ............................ A61K 7/28; C12N 1/00; C12N 9/28; C12N 9/30
(52) U.S. Cl. ...................... 435/202; 435/203; 435/211; 424/50
(58) Field of Search ................................ 435/211, 202, 435/203; 424/50

(56) References Cited

U.S. PATENT DOCUMENTS

| | | | | | |
|---|---|---|---|---|---|
| 4,246,256 | A | * | 1/1981 | Lembke et al. | 424/450 |
| 5,229,277 | A | * | 7/1993 | Day et al. | 435/211 |
| 6,254,856 | B1 | * | 7/2001 | Tsuchiya | 435/211 |

* cited by examiner

*Primary Examiner*—Herbert J. Lilling
(74) *Attorney, Agent, or Firm*—Darby & Darby (57) ABSTRACT

The present invention relates to a dental plaque hydrolyzing or inhibiting enzyme having simultaneously dextranase and amylase activities.

1 Claim, 6 Drawing Sheets

ENZYME CAPABLE OF HYDORLYZING PLAQUE, MICROORGANISM PRODUCING THE SAME, AND A COMPOSITION COMPRISING THE SAME

This application is a 371 of PCT/KR00/00191 filed Mar. 9, 2000.

TECHNICAL FIELD

The present invention relates to an enzyme capable of hydrolyzing dental plaque, a microorganism producing the same and a composition comprising the same.

BACKGROUND OF THE INVENTION

Plaque formed on the surface of a tooth is composed of compactly packed bacteria and non-cellular materials. The main polysaccharide component of plaque is water-insoluble glucan or mutan, which constitutes approximately 20% of the dried mass of plaque and is a main cause of dental caries. Structural studies of glucans produced by Streptococos mutans revealed that the insoluble glucans are mainly composed of α-1,3-, α-1,4-, α-1,6-D-glucoside. Therefore, to eliminate plaque effectively, mutanolytic, amylolytic. and dextranolytic activities are required.

Conventionally, methods of reducing the growth of *Streptococos mutans* (*S. mutans*) in mouth have been suggested to prevent the formation of plaque or dental caries. To achieve this, antiseptics or fluoride which inhibit the growth of *S. mutans* have been added in oral compositions such as toothpaste or mouthwash. Fluoride is one of the most widely used chemicals because it reduces the growth of *S. mutans*. Although fluorine can inhibit the growth of the caries inducing bacteria, it can cause caries-like lesions (formation of orthodontic white spots on tooth enamel) as well as severe side effects such as strong toxicity and air pollution. Enzymes such as dextranase have been used to prevent dental caries, however, its effect has yet to be proven.

U.S. Pat. No. 5,741,773 discloses a toothpaste composition comprising glycomacropeptide having antiplaque and anticaries activities.

These conventional techniques relate to the reduction of the bacteria growth that causes dental caries. This invention can prevent the formation of plaque and hydrolyze pre-formed plaque.

SUMMARY OF THE INVENTION

It is an object of the present invention to provide an enzyme which can hydrolyze or inhibit dental plaque.

Another object of the present invention is to provide a microorganism which produces a dental plaque hydrolyzing or inhibiting enzyme.

The present invention relates to a dental plaque hydrolyzing or inhibiting enzyme, a preparation method thereof, a composition containing the same and microorganism producing the same.

DETAILED DESCRIPTION OF THE PRESENT INVENTION

It has been reported that *Lipomyces starkeyi* (*L. starkeyi*) produces endo-dextranase (EC 3.2.1.11) which degrades dextran and α-amylase which degrades starch. This microorganism has been used in food related applications and is not known to produce antibiotics or toxic metabolites.

Except for a few bacterial dextranases, dextranases which are produced by microorganisms are known to be inducible enzymes. The present inventors have reported that *L. starkeyi* ATCC 74054 produces both dextranase and amylase (U.S. Pat. No. 5,229,277) while disclosing the characteristics of the enzyme produced by the same microorganism. The present inventors have also reported that these microorganisms can produce small molecular weight dextrans by using sucrose and/or starch.

The present invention relates to an enzyme that can inhibit the formation of or degrade dental plaque.

The enzyme of the present invention degrades dextran and starch as well as insoluble glucans and will be referred to as DXAMase hereinafter.

DXAMase according to the present invention mainly produces glucose, isomaltose and branched tetrose and small amounts of branched pentose and hexose when dextran is used as a substrate. When starch is used as a substrate, DXAMase can mainly produce glucose, maltose, maltotriose and maltotetraose as well as a variety of malto-oligosaccharides.

Since DXAMase can degrade levan which is a polymer of β-fructan, DXAMase according to the present invention can effectively degrade fructan forming plaque.

DXAMase according to the present invention, therefore, can effectively degrade soluble as well as insoluble glucans and fructan. DXAMase can effectively prevent dental caries since plaque formation can be inhibited by preventing the aggregation of glucan and microorganisms or pre-formed plaque can be eliminated.

Experimental results using hydroxyapatite, which is similar in composition with dental materials, indicate that DXAMase has a stronger binding with hydroxyapatite than *P. funiculosum* dextranase. Therefore, it is expected that DXAMase will have a higher chance to retain on the tooth surface.

DXAMase according to the present invention is stable in a variety of mouthwash. Moreover, DXAMase does not lose its enzymatic activity in the presence of by chlorhexidine which is currently used as a remedy of periodontal disease.

DXAMase can be isolated from *L. starkeyi* ATCC 74054 or *L. starkeyi* KSM 22. In other words, DXAMase is isolated from a culture medium of *L. starkeyi* ATCC 74054 or *L. starkeyi* KSM 22, and is identified by double bands of 94K and 60K on a SDS-PAGE (10%) eletrophoresis whose pI is 6.0 for both bands.

The present invention also relates to a new microorganism that produces DXAMase. *L. starkeyi* KSM 22 was obtained by mutating *L. starkeyi* ATCC 74054 and has a higher productivity of DXAMase than *L. starkeyi* ATCC 74054. The present microorganism, *L. starkeyi* KSM 22 (Taxonomy: Eukaryota; Fungi; Ascomycota; Saccharomycotina; Saccharomycetes; Saccharomycetales, Lipomycetaceae; Lipomyces; *Lypomyces starkeyi*) has been deposited with Korean Federation of Culture Collections (KFCC) located at Shinchon-dong 134, Seodaemun-ku, Seoul, Korea on Jan. 19, 1999 and was given a deposit number KFCC-11077. The same strain was also deposited according to the Budapest Treaty at the international depository Korean Culture Center of Microorganisms (KCCM) located at 361–221, Yurim B/D, Hongje-1-dong, Seodaemon-gu, Seoul 120–091, Republic of Korea, and was given a deposit number KCCM-10181 on Mar. 7, 2000.

The present invention also relates to a method of producing DXAMase. The method of the present invention comprises culturing *L. starkeyi* ATCC 74054 or *L. starkeyi* KSM 22 and recovering DXAMase from the culture medium.

Since *L. starkeyi* ATCC 74054 and *L. starkeyi* KSM 22 can produce DXAMase from not only the expensive dextran but also relatively cheap glucose, fructose, sucrose or starch, it is economical for practical use. DXAMases obtained from *L. starkeyi* ATCC 74054 and isolated from *L. starkeyi* KSM 22 are practically identical.

Also the present invention relates to an anticaries composition comprising DXAMase. The composition according to the present invention can be used as an additive of a composition for oral hygiene such as toothpaste and mouthwash and food such as candy, chewing gum and beverage. The enzyme according to the present invention maintains its enzymatic activity for a long period of time in commercially available mouthwash solutions and has a strong resistance against enzyme inhibitors. It will be understood that the components of the oral composition and of food ingredients can be verified without difficulties within known conventional limits as will be apparent to those skilled in this art.

Definitions

Dextranase activity is determined by measuring the amount of isomaltose produced by the reaction of an enzyme solution in a buffer solution containing 2% dextran for 15 min at 37° C. Dextranase 1 IU is defined as the amount of the enzyme that produces 1 μmol of isomaltose when reaction is carried out by using dextran as a substrate for 1 min at 37° C.

Amylase activity is measured by reacting the enzyme solution in a buffer solution containing 2% starch for 15 min at 37° C.

Minimum salt medium: $(NH_4)_2SO_4$ 0.5%(w/v); $KH_2PO_4$ 0.1 5%(w/v); $MgSO_4 \cdot 7H_2O$ 0.01%(w/v); NaCl 0.01%(w/v); $CaCl_2 2H_2O$ 0.01%(w/v).

LW medium: yeast extract 0.3%(w/v); $KH_2PO_4$ 0.3%(w/v).

Glucan hydrolysis rate =

$$\frac{\left(\begin{array}{c}\text{reducing sugar produced}\\ \text{with enzyme treatment,}\\ \mu\text{mol/mL}\end{array}\right) - \left(\begin{array}{c}\text{reducing sugar produced}\\ \text{without enzyme treatment,}\\ \mu\text{mol/mL}\end{array}\right)}{\left[\begin{array}{c}\text{total glucose}\\ \text{in polysaccharide}\\ \text{sample, }\mu\text{mol}\end{array}\right]} \times 100$$

Having described the method of this invention, the following figures and examples will serve to further illustrate the method and describe the best mode known to the inventors for carrying out the method, but not limited to the examples given.

EXAMPLE 1

After culturing *L. starkeyi* ATCC 74054 in 1% solution of minimum salt medium supplemented with 0.5% dextran and 0.1% yeast extract for 4 days at 28° C., the cells were suspended in sterilized 100 $\text{mmol}^{-1}$ phosphate buffered saline solution (pH 7.0). After treating 1 ml of cell suspension with 100 μl of ethylmethanesulfonate (EMS) for 5min, 10 min, and 20 min, sodium thiosulfate (10%, w.v) was added. The upper layer of the two layer agar plate consists of minimum salt medium containing 1% starch, 00.5% 2-deoxy-D-glucose and 1.5% agar, and the lower layer consists of blue dextran (0.4% w/v) and 1.5% agar. By observing the degree of formation of transparent circle of blue dextran and performing iodine experiment, a strain that had excellent dextranase as well as amylase activities was selected and named *L. starkeyi* KSM 22.

EXAMPLE 2

*L. starkeyi* KSM 22 was cultured in a 4 L fermentor vessel with LW medium (pH 4.0) containing 1% starch at 30° C. and 100 rpm. After precipitation of 3 L culture supernatant to 300 ml by adding 70% ammonium sulfate, the solution was further concentrated to 50 mL by filtering through a 30 K molecular weight cut-off membrane. The concentrated solution was loaded onto a CM-sepharose column equilibrated with 20 mM potassium phosphate buffer solution (pH 6.0) and eluted with 20 mM potassium phosphate buffer solution (pH 6.0) containing 0.5 M NaCl. The fraction that showed dextranase and amylase activities simultaneously was collected and concentrated by adding isopropanol. Three milliliters of the concentrated solution was loaded onto BIO-RAD A-0.5 column equilibrated with 50 mM citrate phosphate buffer solution (pH 5.5) to perform gel permeation chromatography. The fractions that showed dextranase activity were collected. Two bands at 94 K and 60 K that showed dextranase and amylase activities simultaneously were obtained by performing

EXAMPLE 3

The following 50 mM buffer solutions of pH 2.5~7.5 were used to determine the optimum pH of dextranase and amylase activities of the enzyme obtained in Example 2.

Citrate/phosphate buffer solution (pH 2.5~3.5),
Pyridine acetate buffer solution (pH 4.0~5.5),
Phosphate buffer solution (pH 6.0~7.5).

Figure 1A:
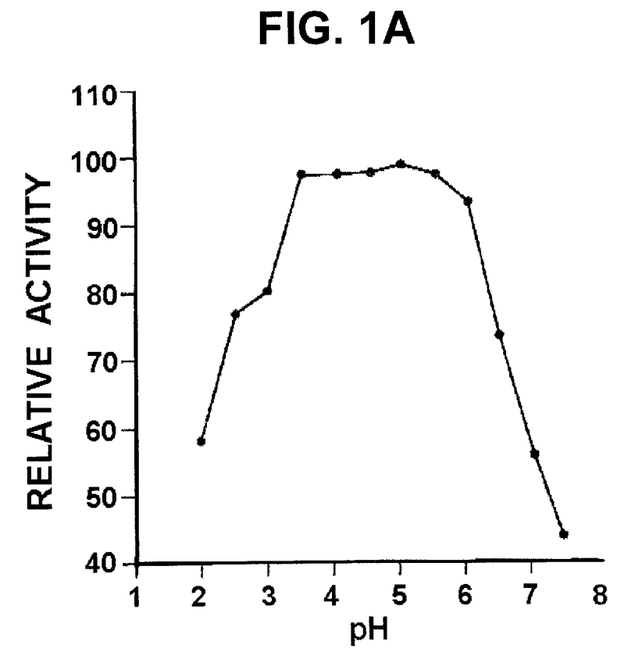
FIG. 1*a* is a graphical representation of the effect of pH on relative amylase activity of DXAMase.
Figure 1B:
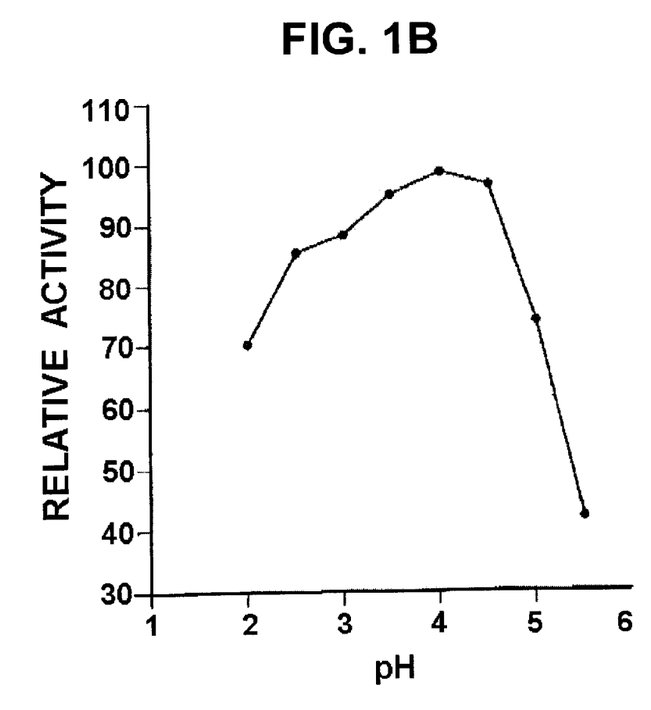
FIG. 1*b* is a graphical representation of the effect of pH on relative dextranase activity of DXAMase.

The results are shown in FIGS. 1*a* and 1*b*. The stability of dextranase activity and amylase activity as a function of pH was measured after reacting the enzyme stock for 72 hours at 22° C. at each pH. Dextranase activity was stable in the pH range of 2.0–7.5 and amylase activity was stable in the pH range of 40~6.0.

Figure 2A:
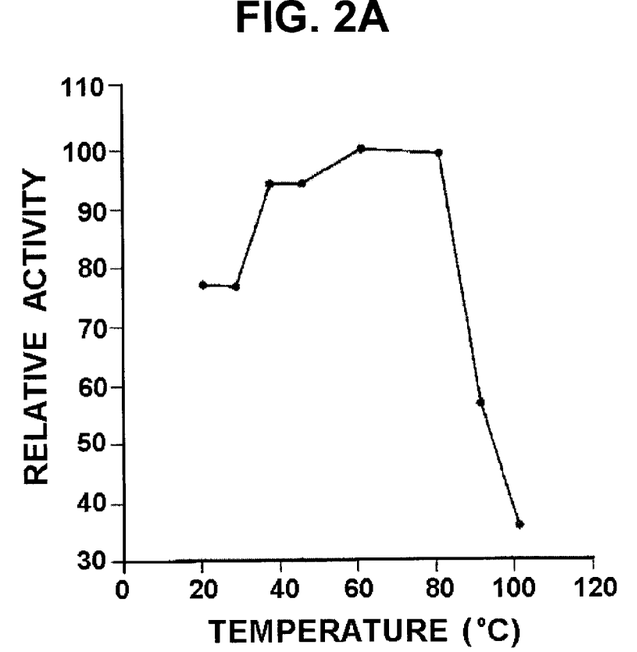
FIG. 2*a* is a graphical representation of the effect of temperature on relative amylase activity of DXAMase.
Figure 2B:
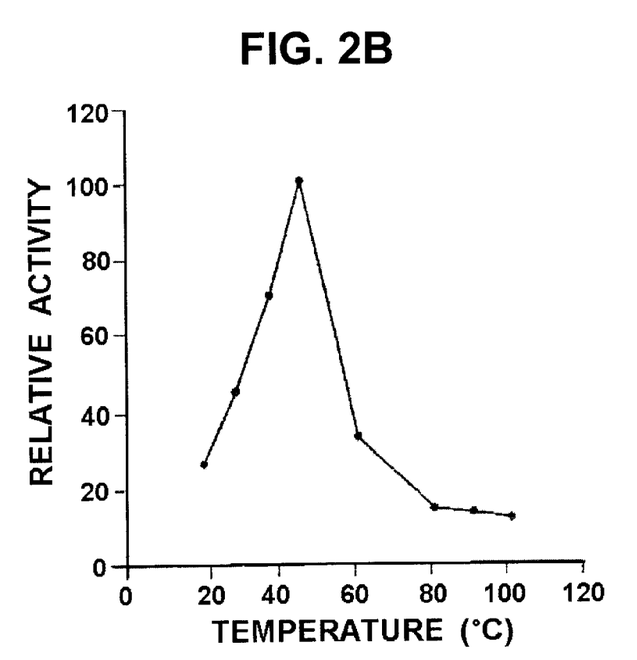
FIG. 2*b* is a graphical representation of the effect of temperature on relative dextranase activity of DXAMase.

To determine the optimum temperature range, dextranase activity and amylase activity were measured after reacting for 15 min in a pH 5.5 buffer solution at different temperatures. The results are shown in FIGS. 2a and 2b. To estimate the temperature stability, the enzyme stock (5 IU) was diluted with a pH 5.5 buffer solution and reacted for 3 min at each temperature before measuring the enzyme activity. At least 80% of the initial dextranase and activity were maintained below 50° C. and 80° C., respectively.

EXAMPLE 4

Hydrolysis of Glucan

Glucosyltransferase isolated from *S. mutans* was used to prepare the following insoluble glucan. After culturing *S. mutans* at 37° C. for 1 day in LW medium (pH 7.0), the supernatant was separated. One liter of the obtained supernatant was mixed with 1 L of 200 mM sucrose solution prepared with 20 mM phosphate buffer solution (pH 7.0) and incubated for 24 hours before centrifuging to collect the insoluble glucan. The insoluble glucan was suspended in citrate-phosphate buffer solution (20 mM, pH 5.5) at the concentration of 5 mg/mL to prepare an insoluble glucan suspension solution.

Also soluble glucan T-2000 (Pharmacia Co. Sweden) was dissolved in citrate-phosphate buffer solution (20 mM, pH 5.5) at 5 mg/mL to prepare soluble glucan solution. In 1 mL of each glucan sample, 5 IU of enzyme obtained in Example 2 was added and reacted for 48 hours at 37° C. The reaction product was identified by TLC. The result is summarized in Table 1. *L. starkeyi* ATCC 74054 was cultured in 4 L of LW medium containing 1% starch and 0.05% deoxy-D-glucose at pH 4.0, 30°C. at an aeration of 1.0 ppm for 72 hours. The enzyme was isolated by using an identical method as in Example 2. The above experiment was repeated by using *L. starkeyi* ATCC 74054. The result is shown in Table 1. The DXAMases produced from *Lipomyces starkeyi* ATCC 74054 and *Lipomyces starkeyi* KSM 22 were almost identical.

Also, dextranase (Sigma) produced by *Penicillium funiculosum* was used to repeat the above experiment. The result is also shown in Table 1.

EXAMPLE 5

Hydrolysis of Levan

Figure 3:
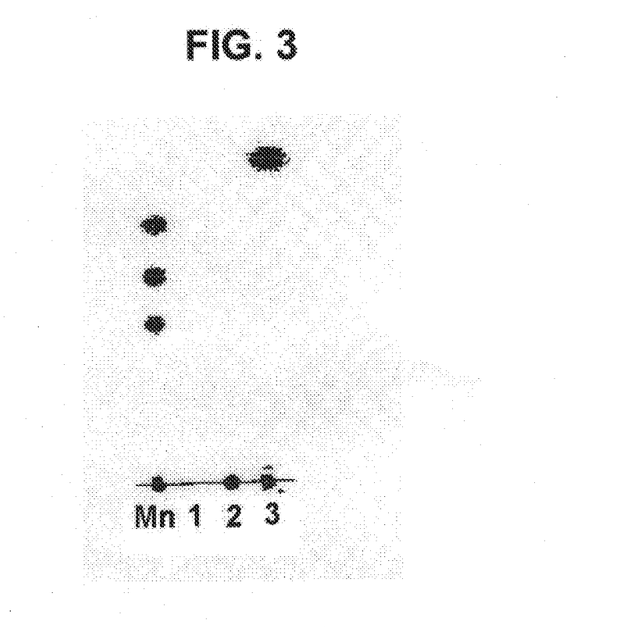
FIG. 3 is a TLC result showing that DXAMase has an ability to degrade levan.

Levan, a β-fructan polymer, was dissolved in a citrate-phosphate buffer solution (20 mM, pH 5.5). DXAMase 1IU was added in 100 μL of levan solution and incubated for 1 hour before identifying the products by TLC. The result is shown in FIG. 3. Since DXAMase according to the present invention can hydrolyze levan, it is expected that DXAMase can effectively degrade fructan that forms plaque.

EXAMPLE 6

Inhibition of Cell Aggregation by Glucan

Figure 4:
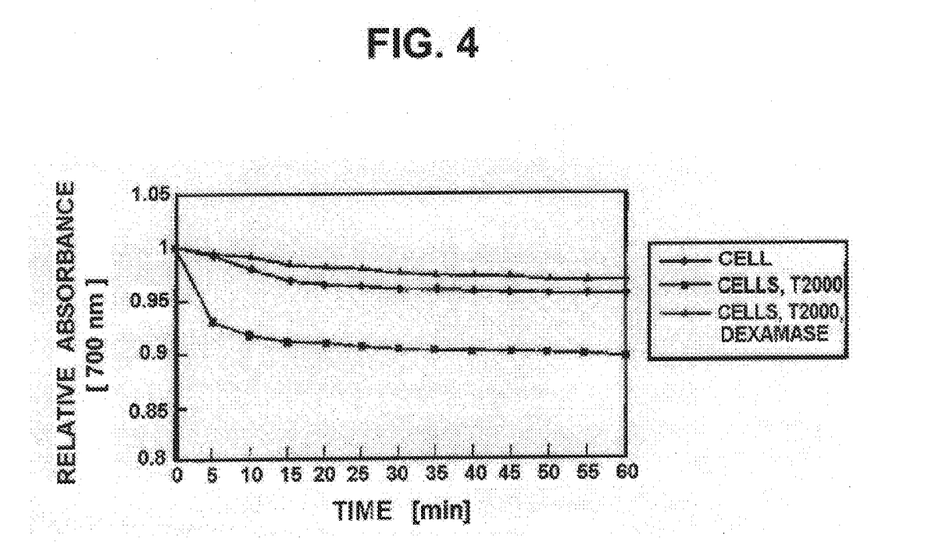
FIG. 4 is a graphical representation of the prevention of cell aggregation by DXAMase.

The following experiment was performed to observe the cell aggregation by glucan. In 100 mL of tryptic soy broth containing 0.25% glucose, *S. mutans* was inoculated and cultivated overnight at 37° C. Cells were harvessted by centrifugation and washed twice with 5 mM Tris buffer (pH 8.4). The washed cells were suspended in an equal volume of identical buffer solution as the medium. The mixture of 550 μL of cell suspension and 50 μL of water-soluble glucan T2000 (dissolved to a concentration of 15 g/mL in 5 mM Tris buffer (pH 8.4)) was treated with 50 μL of DXAMase (0.5 IU/ml). After incubating at 40° C. for 5 min, the absorbance of the mixture was measured at 5-minute intervals for 60 minutes at $A_{700}$. The absorbance decreased as aggregation between cell and soluble glucan T2000 progressed. When compared to the control without DXAMase, the degree of aggregation was prohibited by treating with 50 μL of DXAMase (0.5 IU/ml). The result is shown in FIG. 4.

EXAMPLE 7

Plaque Inhibiting and Eliminating Effect

This experiment was performed by following the method of Schachtele C. F., (Infect. Immun. 1975, 12; 309–317) as follows.

*S. mutans* suspension solution was prepared by following the method as in Example 5 except that the cultured and collected cells were suspended at 5%(wet w/v) in a sterile deionized water. To a glass tube, 0.2 mL of cell suspension,

TABLE 1

| Percent Hydrolysis | | glucose | Isomaltrose | Isomaltotriose | Branched maltotetraose | Branched maltopentaose | Nigerose |
|---|---|---|---|---|---|---|---|
| ATCC 74054 | | | | | | | |
| Soluble glucan | 65.7 | 30 | 31 | 15 | 5 | 3 | |
| Insoluble glucan | 18.9 | 80 | | | | | |
| KSM 22 | | | | | | | |
| Soluble glucan | 76.8 | 30 | 31 | 15 | 5 | 3 | |
| Insoluble glucan | 19.5 | 80 | | | | | |
| Penicillium | | | | | | | |
| Soluble glucan | 66.7 | 22 | 49 | | 7 | 8 | |
| Insoluble glucan | 5.2 | 22 | 20 | | 6 | | 11 |

Figure 5:
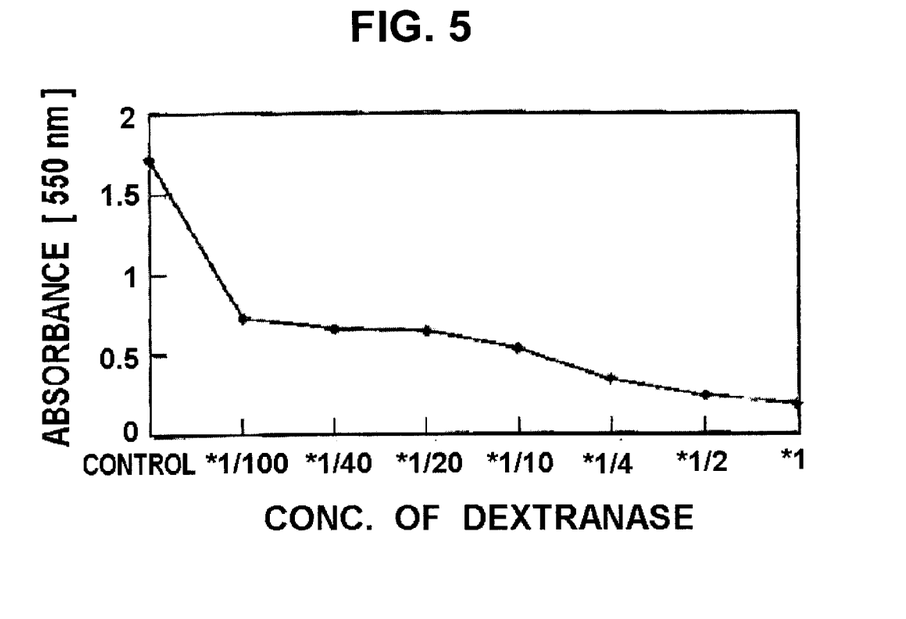
FIG. 5 is a graphical representation of the prevention of plaque formation as a function of DXAMase concentration.

1.0 mL of sucrose solution (concentration of 50 mg/ml dissolved in 100 mM phosphate buffer solution (pH 5.8)), 4.4 mL of sterile deionized water and 0.4 mL DXAMase (equilibrated with 50 mM phosphate buffer solution (pH 5.8)) were added and reacted at 37° C. for 16~18 hours without stirring. The amount of DXAMase was 0~2 IU/mL. After carefully removing reaction solution and cells that were not attached, the attached cells were washed with 20 mM phosphate buffer solution (pH 5.8) and suspended by adding 6.0 mL of the identical buffer solution. The turbidity was measured at $A_{550}$. The result is shown in FIG. 5. When compared to the control without DXAMase, 80% of insoluble glucan formation was prohibited by treating with 0.1 IU/mL of DXAMase (FIG. 5).

Figure 6:
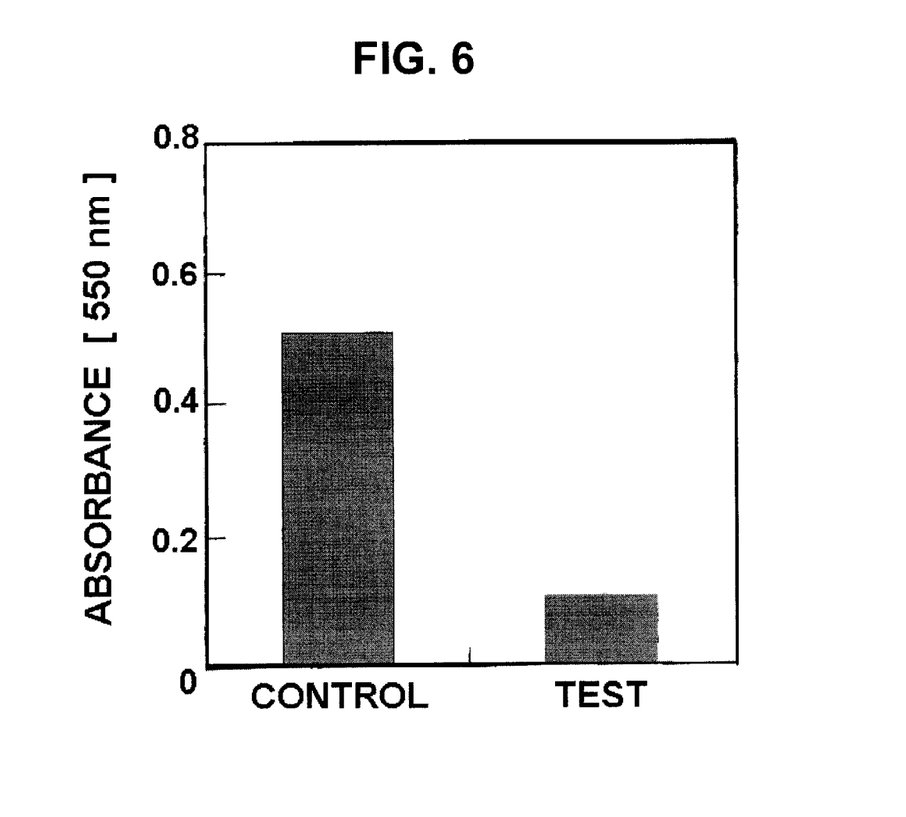
FIG. 6 is a bar graph representing that DXAMase can remove the pre-formed plaque.

To observe whether DXAMase can eliminate pre-formed glucan layer, attachable material consisting of glucan layers was obtained by using the same method as above except the fact that DXAMase was not added. On these attachable cells, 0.5 IU/mL of DXAMase was added and incubated for 24 hours at 37° C. After carefully removing reaction solution and cells that were not attached, the absorbance was measured at $A_{550}$ to determine the amount of attachable material. When compared to the control without DXAMase, approximately 80% of the attachable film was degraded (FIG. 6).

EXAMPLE 8

Binding Effect on Tooth Surface

To confirm the binding effect of DXAMase on the tooth surface, the following experiment was performed. Hydroxyapatite (Bio-Gel HTP, Bio-Rad Laboratories) was suspended in 10 mM phosphate buffer solution (pH 6.8) and packed in a 1.2×5 cm column. In each column, 2 mL(10 IU/ml) of *P. funiculosum* dextranase (Sigma) dissolved in 10 mM $KH_2PO_4$(pH 6.8) was loaded. Solutions were eluted by using 10 mM~0.5M phosphate buffer solutions (pH 6.8 for all) to collect 1 ml fractions. In each fraction, both dextranase activity and amylase activity were measured. Identical experiment was also carried out by using DXAMase.

*P. funiculosum* dextranase exhibited at least 2 peaks, and these two dextranases did not bind on hydroxyapatite and were eluted by 25 mM phosphate buffer solution. In contrast, dextranase activity in the case of DXAMase was eluted by 50, 125, 225 mM phosphate buffer solution, and amylase activity in the case of DXAMase was eluted by 125, 225, 355 mM phosphate buffer solution. From this result, DXAMase is expected to have a higher binding effect on the tooth surface than *P. funiculosum* dextranase.

Instead of hydroxyapatite, saliva-coated hydroxyapatite was used to carry out the experiment by loading DXAMase of the present invention. Saliva-coated hydroxyapatite was prepared as follows. After collecting saliva from male and female in their 20's and centrifuging to prepare clear solution, the solution was further filtrated (Whatman, 0.2 µm). One milliliter of the prepared saliva was mixed with 1 g of hydroxyapatite and incubated for 1 hour. After removing the supernatant by centrifugation and washing with phosphate buffer solution, saliva-coated hydroxyapatite was prepared. DXAMase activity was eluted by using 200–300 mM phosphate buffer solution.

EXAMPLE 9

Plaque Inhibiting and Eliminating Effect (Co-use with Mouthwash Solution)

Figure 7:
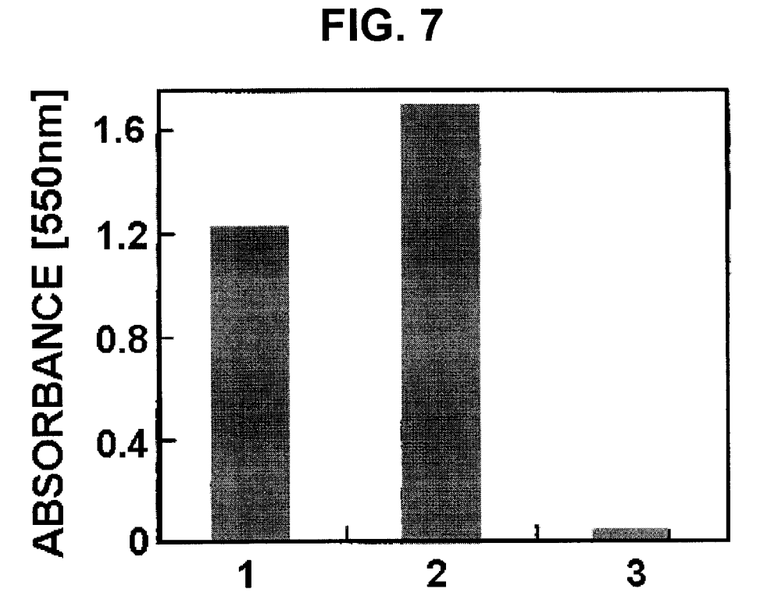
FIG. 7 is a bar graph representing that DXAMase in mouthwash can prevent glucan formation.

Into a commercially available mouthwash solution product A(Johnson & Johnson), 5 IU/mL of DXAMase obtained from Example 2 was added. Into a glass tube, 0.2 mL of *S. mutans* suspension obtained by using the method as in Example 4, 1.0 mL of sucrose solution (dissolved at 50 mg/ml in 100 mM phosphate buffer solution (pH 5.8)), 4.4 mL of sterile deionized water and 0.4 mL DXAMase (50 mM phosphate buffer solution (pH 5.8)) were added and reacted at 37° C. for 16~18 hours without stirring. After carefully removing reaction solution and cells that are not attached, the attached cells were washed with 20 mM phosphate buffer solution (pH 5.8) and suspended by adding 6.0 mL of the identical buffer solution. The turbidity was measured at $A_{550}$. When compared to the control having mouthwash solution without DXAMase, the formation of insoluble glucan with mouthwash solution containing DXAMase was prohibited by 80%. The result is shown in FIG. 7. (1: sucrose+*S. mutans* suspension 0.2 mL, 2: sucrose+*S. mutans* suspension+mouthwash, 3: sucrose+*S. mutans*+DXAMase, mouthwash).

Figure 8:
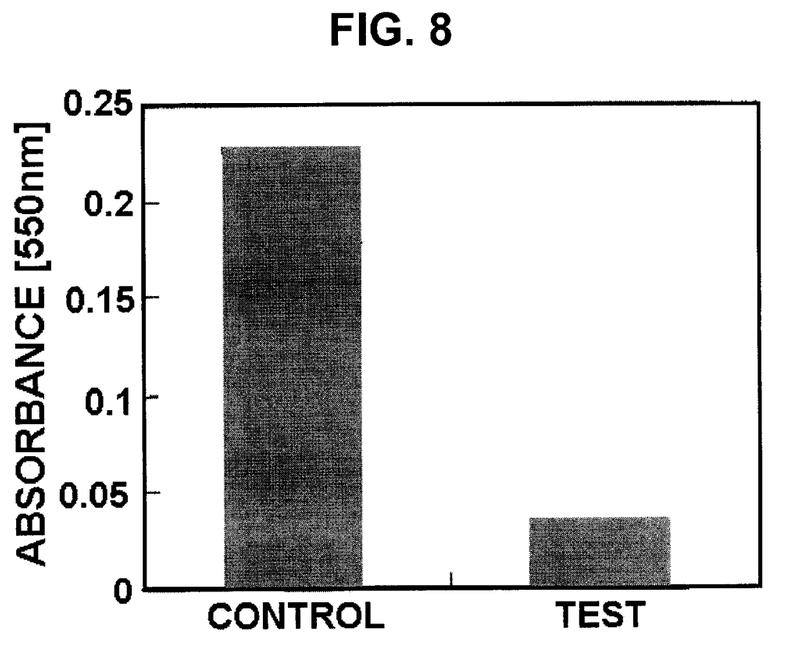
FIG. 8 is a bar graph representing that DXAMase in mouthwash can remove the pre-formed insoluble glucan.

To evaluate the removable effect of pre-formed glucan layers, attachable cells wherein glucan layer is formed was obtained by using the same method as above except that DXAMase was not added. On these attachable cells, 1 mL of mouthwash solution containing 5 IU/mL of DXAMase was added and incubated for 24 hours at 37° C. After carefully removing reaction solution and cells that were not attached, the absorbance was measured at $A_{550}$ to determine the amount of the attachable material. When compared to the control with mouthwash solution product A without DXAMase, approximately 80% of the attachable film was degraded. The result is shown in FIG. 8.

EXAMPLE 10

Stability Test

To test the stabilization of dextranase and amylase activities of DXAMase by chemicals comprising mouthwash solution, the enzyme activity was measured in the presence of the enzyme inhibitors and chemicals in the mouthwash solutions in Table 2. In 1 mL of each chemical solution, 5 IU of DXAMase was added and reacted for 5 min at 37° C. Reaction was further carried out by adding 2% dextran or starch of an equal volume. Enzyme activity was measured by using a cupper-bicinchoninate reduction number method (Jeffrey D. Fox et al., Analytical Biochemistry 195, 93–96 (1991)). The result is summarized in Table 2. The enzymatic activity did not decrease by various components comprising the mouthwash or by chlorhexidine, which is mainly used to treat periodontal disease.

TABLE 2

| | | Relative activity (%) *Lipomyces starkeyi* KSM 22 | |
|---|---|---|---|
| Enzyme inhibitor | Concentration | Dextranase | Amylase |
| Control group | | 100 | 100 |
| EDTA | 10 mM | 100 | 100 |
| SDS | 0.05% | 91 | 92 |
| | 0.5% | 85 | 68 |
| Fluoride | 0.05% | 94 | 91 |
| Ethanol | 1% | 99 | 100 |
| | 5% | 98 | 98 |
| | 10% | 98 | 97 |
| | 20% | 97 | 97 |
| Sodium benzoate | 1% | 100 | 100 |
| Propylene glycol | 1% | 100 | 100 |
| Chlorhexydine | 0.01% | 98 | 98 |
| | 0.02% | 98 | 97 |
| | 0.05% | 97 | 97 |
| | 0.1% | 93 | 96 |

TABLE 2-continued

| Enzyme inhibitor | Concentration | Relative activity (%) Lipomyces starkeyi KSM 22 ||
| --- | --- | --- | --- |
| | | Dextranase | Amylase |
| Cetylpyridinium chloride | 0.001% | 100 | 100 |
| | 0.01% | 99 | 95 |
| | 0.05% | 94 | 87 |
| | 0.1% | 88 | 80 |
| | 0.5% | 71 | 62 |
| | 1% | 67 | 56 |

EXAMPLE 11

Figure 9:
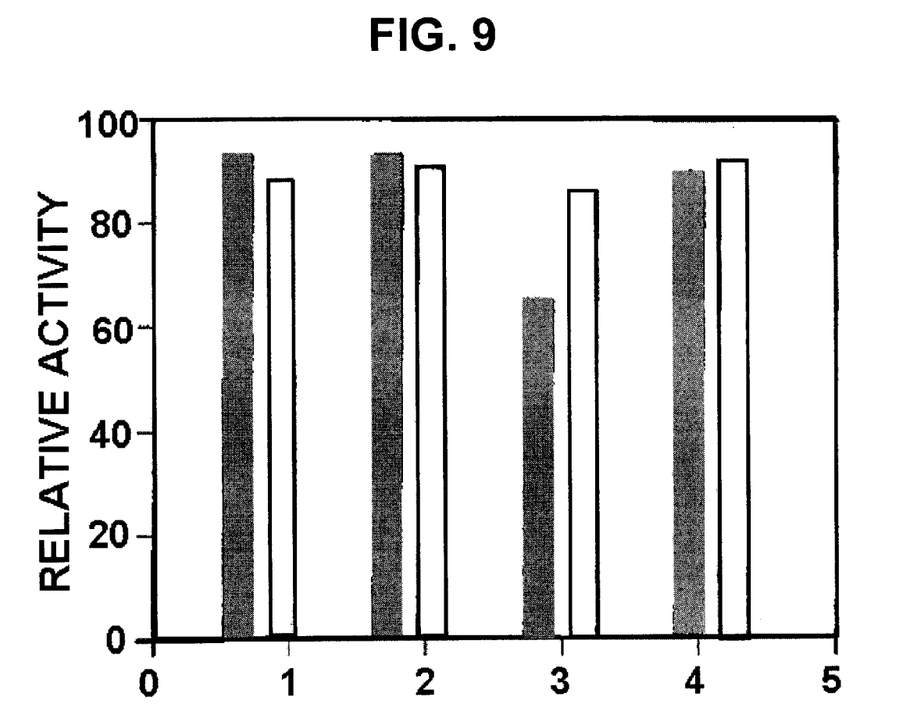
FIG. 9 is a bar graph representing the stability of DXAMase in a commercially available mouthwash solution.

In 4 different commercially available mouthwash solutions, 10 mg/ml of DXAMase, prepared as in Example 2, was added to observe the stability of the enzyme for a 6 month period. The result is shown in FIG. 9. (A: Johnson & Johnson, USA, B: Hanmi Pharmaceutical Co., Korea, C: DongA Pharmaceutical Co., Korea, D: II-Dong Pharmaceutical Co., Korea). After 6 months, at least 93% of initial dextranase and amylase activities were maintained. (■: dextranase activity, □: amylase activity). Also, in an A oral composition and a B oral composition, more than 90% of initial activity was maintained after 10 months, and more than 73% of initial activity was maintained after 22 months.

According to the present invention, a new enzyme that has amylase activity and dextranase activities is provided. Also, the present invention provides an oral composition with an excellent antiplaque and anticaries activities.

What is claimed is:

1. An enzyme having antiplaque and anticaries activities, having a molecular weight of 94K measured by SDS-PAGE, having a dextranase and amylase activities simultaneously and degrading insoluble glucans, wherein the enzyme is isolated from *L. starkeyi* KSM 22.

* * * * *